(12) United States Patent
Zubrin et al.

(10) Patent No.: US 9,725,386 B2
(45) Date of Patent: Aug. 8, 2017

(54) SYSTEMS AND METHODS FOR MANUFACTURE OF METHANOL FROM NATURAL GAS AND FLARE GAS FEEDSTOCK

(71) Applicant: Pioneer Energy Inc., Lakewood, CO (US)

(72) Inventors: Robert M Zubrin, Golden, CO (US); Boris Nizamov, Highlands Ranch, CO (US); Thomas L Henshaw, Monument, CO (US); Adam M Kortan, Arvada, CO (US); James Siebarth, Lakewood, CO (US); Colin Apke, Castle Rock, CO (US); Mark Berggren, Golden, CO (US)

(73) Assignee: Pioneer Energy, Inc., Lakewood, CO (US)

( * ) Notice: Subject to any disclaimer, the term of this patent is extended or adjusted under 35 U.S.C. 154(b) by 0 days.

(21) Appl. No.: 15/447,066

(22) Filed: Mar. 1, 2017

(65) Prior Publication Data
US 2017/0174592 A1    Jun. 22, 2017

Related U.S. Application Data

(60) Division of application No. 15/043,558, filed on Feb. 13, 2016, now Pat. No. 9,637,433, which is a
(Continued)

(51) Int. Cl.
*B01J 8/00* (2006.01)
*B01J 8/02* (2006.01)
(Continued)

(52) U.S. Cl.
CPC ......... *C07C 29/1518* (2013.01); *B01J 8/0492* (2013.01); *B01J 8/0496* (2013.01);
(Continued)

(58) Field of Classification Search
CPC ..... B01J 8/00; B01J 8/02; B01J 8/0278; B01J 8/04; B01J 8/0492; B01J 8/0496;
(Continued)

(56) References Cited

U.S. PATENT DOCUMENTS 6,444,712 B1    9/2002    Janda
8,440,868 B2    5/2013    Stauffer
(Continued)

OTHER PUBLICATIONS

M. S. Spencer, "The role of zinc oxide in Cu/ZnO catalysts for methanol synthesis and the water-gas shift reaction," Topics in Catalysis 8, pp. 259-266, 1999.

*Primary Examiner* — Natasha Young
(74) *Attorney, Agent, or Firm* — American Patent Agency PC; Daniar Hussain; Xiaomeng Shi

(57) ABSTRACT

A mobile system and method that reform flare gas, methane, or natural gas, using air without steam, to directly produce methanol, a clean burning gasoline blend, component, and/or substitute are disclosed. The system first reforms the air-methane mixture at ambient atmospheric pressure, then compresses the resulting CO-hydrogen-nitrogen gas mixture to about 600 psi, and feeds it through a methanol reactor which reacts the gas mixture directly into methanol. The nitrogen is returned by the system back to the atmosphere. Methanol is a clean burning gasoline substitute, and can be used to displace significantly costlier and dirtier petroleum-based fuel, while solving a critical problem with flaring. For example, the over 120 billion cubic feet per year that was flared in North Dakota in 2014 could be converted into over 6 million tons of methanol.

26 Claims, 11 Drawing Sheets

| Fig. 1A<br>SYNGAS GENERATION | Fig. 1B<br>METHANOL SYNTHESIS<br>(OPTION 1) | Fig. 1C<br>METHANOL SYNTHESIS<br>(OPTION 2) |
|---|---|---|

Related U.S. Application Data continuation-in-part of application No. 14/953,268, filed on Nov. 27, 2015, now Pat. No. 9,643,906.

(60) Provisional application No. 62/085,391, filed on Nov. 28, 2014.

(51) Int. Cl.

| | |
|---|---|
| *B01J 8/04* | (2006.01) |
| *B01J 19/00* | (2006.01) |
| *B01J 19/24* | (2006.01) |
| *C01B 3/00* | (2006.01) |
| *C01B 3/02* | (2006.01) |
| *C01B 3/32* | (2006.01) |
| *C01B 3/34* | (2006.01) |
| *C01B 3/36* | (2006.01) |
| *C01B 3/38* | (2006.01) |
| *C07C 29/151* | (2006.01) |
| *F02B 5/02* | (2006.01) |
| *F02B 63/04* | (2006.01) |
| *F02M 21/02* | (2006.01) |
| *C07C 29/00* | (2006.01) |
| *C07C 29/15* | (2006.01) |
| *C07C 31/00* | (2006.01) |
| *C07C 31/04* | (2006.01) |
| *C07C 41/00* | (2006.01) |
| *C07C 41/09* | (2006.01) |
| *C07C 41/42* | (2006.01) |
| *C07C 43/04* | (2006.01) |

(52) U.S. Cl.
CPC ............... *B01J 19/245* (2013.01); *C01B 3/38* (2013.01); *F02B 5/02* (2013.01); *F02B 63/04* (2013.01); *F02M 21/0206* (2013.01); *B01J 2219/24* (2013.01); *C01B 2203/0233* (2013.01); *C01B 2203/061* (2013.01); *C01B 2203/0805* (2013.01); *C01B 2203/0883* (2013.01); *C01B 2203/1241* (2013.01); *C01B 2203/1258* (2013.01); *C01B 2203/84* (2013.01)

(58) Field of Classification Search
CPC . B01J 19/00; B01J 19/24; B01J 19/245; B01J 2208/00; B01J 2208/02; B01J 2208/023–2208/025; B01J 2219/24; Y02P 20/00; Y02P 20/10; Y02P 20/12; Y02P 20/121; Y02P 20/125; C01B 3/00; C01B 3/02; C01B 3/32; C01B 3/34; C01B 3/36; C01B 3/38; C01B 3/382; C01B 2203/00–2203/0205; C01B 2203/0227; C01B 2203/0233; C01B 2203/0244; C01B 2203/025; C01B 2203/0266; C01B 2203/06; C01B 2203/061; C01B 2203/10; C01B 2203/1041; C01B 2203/1076; C01B 2203/12–2203/1211; C01B 2203/1235; C01B 2203/1241; C01B 2203/1256; C01B 2203/80; C01B 2203/84; C07C 29/00; C07C 29/15; C07C 29/151; C07C 29/1516; C07C 29/1518; C07C 31/00–31/04; C07C 41/00; C07C 41/01; C07C 41/09; C07C 41/34; C07C 41/40; C07C 41/42; C07C 43/00–43/043; F02B 5/00; F02B 5/02; F02B 63/00; F02B 63/04; F02M 21/00–21/0206
See application file for complete search history.

(56) References Cited

U.S. PATENT DOCUMENTS

| | | |
|---|---|---|
| 8,551,444 B2 | 10/2013 | Agnihotri et al. |
| 8,835,517 B2 | 9/2014 | Cheiky et al. |
| 2008/0033066 A1 | 2/2008 | Haynes |
| 2010/0163804 A1 | 7/2010 | Schenck |
| 2012/0088850 A1 | 4/2012 | Rabovitser et al. |
| 2012/0103611 A1 | 5/2012 | Brandl et al. |
| 2013/0058855 A1 | 3/2013 | Toppinen et al. |
| 2013/0116347 A1* | 5/2013 | Cheeley ............... C10K 3/026 518/705 |

* cited by examiner

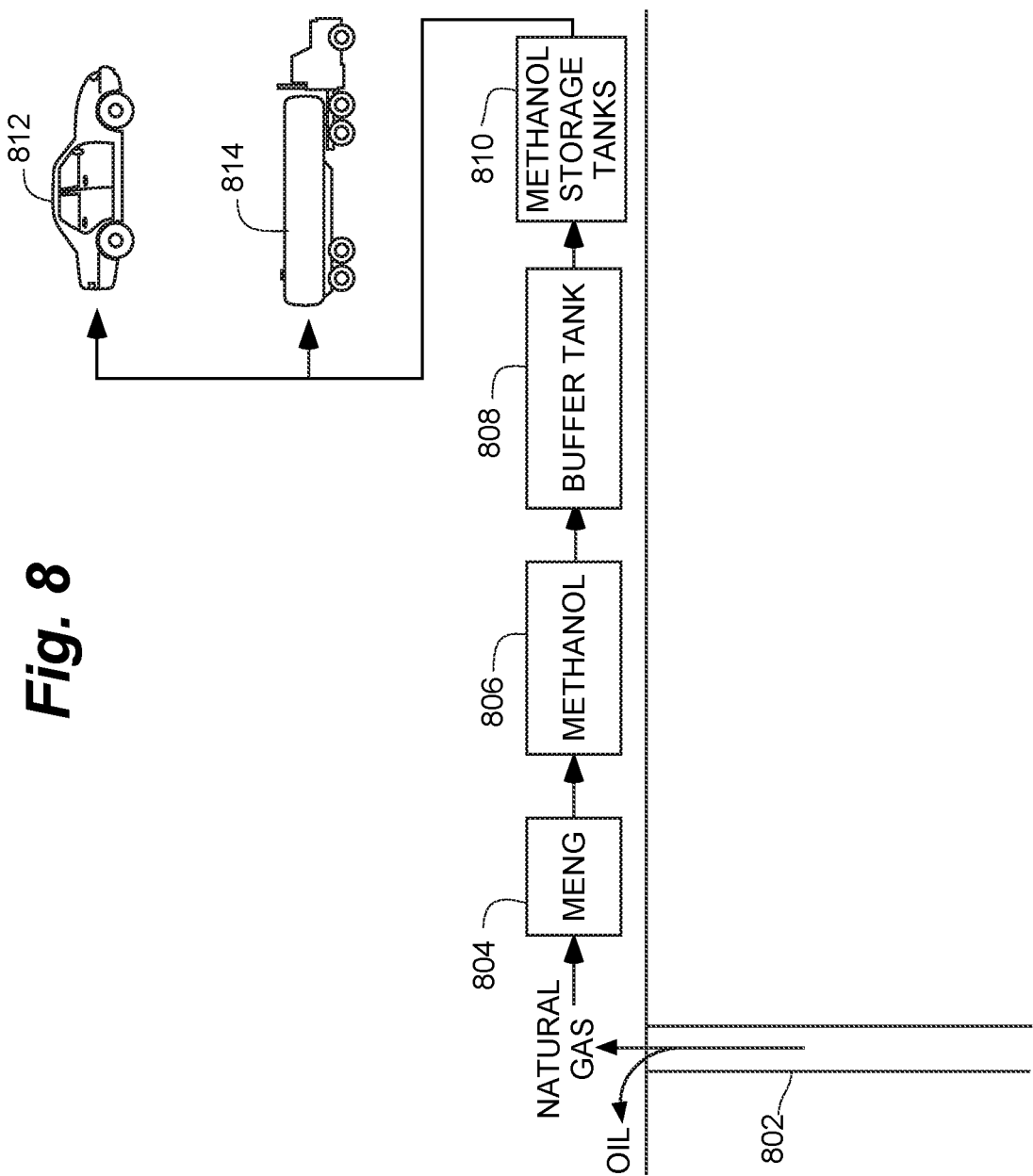

SYSTEMS AND METHODS FOR MANUFACTURE OF METHANOL FROM NATURAL GAS AND FLARE GAS FEEDSTOCK

REFERENCE TO RELATED APPLICATIONS

This application is a divisional of and claims the benefit of priority to co-pending application U.S. Ser. No. 15/043,558, now U.S. Pat. No. 9,637,433, filed on 13 Feb. 2016, and entitled "SYSTEMS AND METHODS FOR MANUFACTURE OF METHANOL FROM NATURAL GAS AND FLARE GAS FEEDSTOCK," which itself is a Continuation-In-Part (CIP) and claims the benefit of priority from U.S. Ser. No. 14/953,268, now U.S. Pat. No. 9,643,906, filed on 27 Nov. 2015, and entitled "SYSTEMS AND METHODS FOR MANUFACTURE OF DIMETHYL ETHER (DME) FROM NATURAL GAS AND FLARE GAS FEEDSTOCK," which itself is a non-provisional of and claims the benefit of priority from provisional application U.S. Ser. No. 62/085,391, filed on 28 Nov. 2014, and entitled "DIMETHYL ETHER (DME), A DIESEL-SUBSTITUTE LIQUID FUEL, FROM NATURAL GAS AND FLARE GAS FEEDSTOCK," all of which are hereby incorporated by reference in their entireties herein.

FIELD OF THE INVENTION

The present invention relates to enabling the utilization of raw natural gas, such as flare gas, stranded gas, associated gas, and so on, for methanol production. More specifically, this invention relates to a mobile system for producing methanol from any natural gas feedstock, wet or dry.

BACKGROUND OF THE INVENTION

The statements in this section merely provide background information related to the present disclosure and may not constitute prior art.

The U.S. is currently flaring so much stranded natural gas that the gas flares are visible from outer space. The world annually flares about 5,000 billion cubic feet (BCF) of stranded gas. This is equivalent to the annual gas usage of France and Italy combined, and represents about 5% of the world's gas production. It is estimated that in North Dakota alone, where oil production from fracking reached 1 million barrels per day, around 36% of North Dakota's associated gas was flared in 2014—about 120 BCF/yr. All this flare gas produces significant quantities of $CO_2$ emissions, estimated to be about 7 million tons of $CO_2$-equivalents in emissions from North Dakota's flaring, or the emissions from about 1.3 million cars, while producing no useful product. Furthermore, North America is facing a vast abundance of natural gas generally, driving natural gas prices to historical lows, making it an ideal feedstock for liquid fuel production.

Flaring of natural gas entails significant loss of income for oil and gas producers that could be earned by selling the natural gas product. Still more financial losses are entailed by failing to make use of the energy content of the flared gas to generate power. As a result, such producers must buy their electric power from the grid, or even worse, generate it themselves at significant cost (typically USD$0.40/kWh) using on-site diesel generators consuming expensive diesel fuel. Furthermore, the large-scale flaring of natural gas has raised environmental issues that could cause state and/or federal regulators to act to fine, shutdown, or highly regulate their operations.

The United States oil and gas industry annually flared approximately 7.1 billion cubic meters (bcm), or 250 billion cubic feet (bcf) in 2011 (Source: Global Gas Flaring Reduction Partnership, *Estimated Flared Volumes from Satellite Data*, 2007-2011, 2013). "Flaring will escalate as oil producers approach the milestone of 1 million barrels a day from the Bakken formation, a 360-million-year-old shale bed two miles underground. About 10,100 wells produced 29 million barrels of oil in January 2014, according to the North Dakota Industrial Commission. Drillers flared 340 million cubic feet (mmcf), or 34 percent, of the 1 billion cubic feet of natural gas produced per day in January 2014, about twice as much as the 184 million cubic feet burned per day in 2011, said Marcus Stewart, an analyst at Denver-based Bentek Energy. 'The lost revenue adds up to $1.4 million each day,' said Stewart. Energy executives say economic realities force them to start producing oil from wells before infrastructure is in place to haul away less-valuable natural gas." (Source: Jennifer Oldham, *A Landscape of Fire Rises Over North Dakota's Gas Fields*, Bloomberg News, Apr. 7, 2014)

Canada also has a significant flaring problem. It is estimated that Canada flared 2.4 billion $m^3$ per year in 2011 (Source: Global Gas Flaring Reduction Partnership, *Estimated Flared Volumes from Satellite Data*, 2007-2011, 2013.) It is estimated that the Canadian province of Alberta alone flared 868 million $m^3$ and vented another 333 million $m^3$ in 2007. (Source: Bott, R. D., *Flaring Questions and Answers*, 2nd ed., Canadian Centre for Energy Information, 2007.) A similar situation holds around the world, with significant quantities of gas flared in Russia, Nigeria, and other parts of the world.

This flaring produces significant quantities of $CO_2$ emissions while producing no useful product. If this waste flare gas could be utilized for powering transportation vehicles, used to produce liquid fuel, and/or transported for sale to market, significant environmental and economic benefits would accrue.

Furthermore, gas produced as a by-product of fracking shale for oil is often rich in natural gas liquids (NGLs), including but not limited to in the Bakken formation of North Dakota, United States. Although natural gas prices are at a historic low in the United States, the high concentration of NGLs justifies gathering and processing the gas. However, as gas gathering infrastructure is put into place, and statutory restrictions kick in after 12 months after initial drilling, flaring on old wells may be reduced. Unfortunately, newly drilled wells as well as wells far from pipeline infrastructure will continue to be flared. This high variability and uncertainty in flaring quantities make it extremely difficult to plan and effectively size traditional gas gathering and pipeline infrastructure to minimize flaring.

It is highly financially and environmentally disadvantageous to flare valuable natural gas that could be sold for profit. It is even more financially and environmentally disadvantageous to utilize large quantities of gasoline for transportation vehicles while at the same time flaring a feedstock that could be doing the same job. The problem is that liquids-rich raw natural gas cannot be used in gasoline engines directly, and cannot be easily transported by truck.

Therefore, there exists an important need for a solution to address the problem of utilizing raw natural gas (wet or dry), which may have significant quantities of NGLs, to the maximum extent and to minimize or eliminate flaring, while still meeting the operators' requirements of a highly variable and uncertain flow rate in the raw natural gas stream.

Accordingly, as recognized by the present inventors, what are needed are a novel method, apparatus, and system for converting raw natural gas into a liquid stream that can be easily transported by truck, and that can be utilized for transportation and/or power generation, or for other purposes in existing equipment. As recognized by the present inventors, what is also needed is a liquid fuel synthesis system that is compact, portable, and modular, and which can be easily and quickly delivered to, as well as removed from, flare gas sites as flaring volumes change and as natural gas infrastructure matures.

Therefore, it would be an advancement in the state of the art to provide an apparatus, system, and method for producing a liquid fuel from a raw natural gas source at or near an oil or gas site that flares its associated gas. It would also be an advancement in the state of the art to provide a compact, portable, and modular liquid fuel production apparatus.

It is against this background that various embodiments of the present invention were developed.

BRIEF SUMMARY OF THE INVENTION

Whereas the problem of flare gas was previously recognized, two known solutions included (1) pipelines to transport the raw natural gas to natural gas plants/refineries, and (2) mobile systems to process the flare gas on-site. These will be briefly discussed in turn. First, pipelines can be built to transport the raw natural gas from oil fields currently flaring to natural gas plants/refineries. This has several drawbacks, including complexity, cost, long-lead time, and permitting issues associated with building pipelines. An additional problem with pipelines is the flare volumes are highly uncertain and variable, making it difficult to plan pipeline construction. Additionally, pipelines cannot be deployed quickly to address the existing problem in real-time, nor can they be moved when flare volumes decrease. Finally, even if pipelines could be built, natural gas plants are highly expensive and large, capital-intensive infrastructure that would take time and large capital to finance and build.

Secondly, existing mobile systems have many shortcomings; all existing mobile systems are designed to either capture NGLs or produce dry generator gas. Some existing mobile systems are designed for extracting NGLs from the raw natural gas, and then flare the remaining methane and ethane because it is unusable in existing gensets. Other existing mobile systems generate high-quality (lean) methane for CNG production or pipelines, and flare the remaining NGLs because it has high ethane content (and hence a high vapor pressure), and cannot be transported in existing tanks. Many mobile systems utilize the Joule-Thompson (J-T) effect, and cannot remove a substantial portion of the ethane content in the flare gas, resulting in a gas mixture that is unpractical to use in existing, unmodified gensets. The system design presented in the present application solves the problems with both existing pipeline-based solutions as well as existing mobile systems by producing a transportable fuel from the raw natural gas feedstock.

The MEthanol from Natural Gas ("MENG") system would allow methanol, a clean burning fuel, to be produced from currently wasted flare gas, at a cost substantially lower than petroleum-based gasoline. Methanol can be used at 100% substitution on a regular gasoline engine, with small modifications to the fuel line on the engine. Methanol is a sulfur-free, particulate-free, ultra-clean liquid fuel, that can be put directly to use without further refinement. Using flare gas and surplus natural gas for liquid fuel production yields significant environmental and economic benefits. This process would enhance the economic and energy security of the world through: a) reductions of imports of energy from volatile regions of the world; b) reductions in energy-related emissions, including greenhouse gases; and c) improvement in the energy and economic efficiency of the oil and gas sector.

Methanol became popular as an automotive fuel within California during the 1970s following the oil embargos, though race teams have been using it for over a half century. When burned in an internal combustion engine, the overall efficiency is improved and the EPA regulated emissions are greatly reduced. Furthermore, an increase in fuel mileage over gasoline blends is possible by fully utilizing methanol's 110 octane rating in a high-compression motor. Vehicles do not need to be methanol-specific, since software exists that allows the engine to adapt to blends of methanol, ethanol, butanol, or gasoline, or mixtures thereof.

Methanol has low health risks as evidenced by the fact that hundreds of millions of drivers routinely handle methanol as a component of window-washing fluid. Methanol is biodegradable and does not harm the environment. One drawback of methanol is that the energy content of a gallon of methanol is approximately half of the energy content of a gallon of gasoline, but this is compensated for by its low production cost from natural gas.

The inventors have thus developed a unique design for a mobile system that reforms flare gas or natural gas, using air without steam, to directly produce methanol. The system first reforms the natural gas and air mixture at 1 bar, and then compresses the resulting CO-hydrogen-nitrogen gas mixture to 600 psi and feeds it through a methanol reactor to produce methanol vapor. No separation system is required after the methanol reactor since methanol has a low vapor pressure and can be easily condensed to liquid at ambient temperatures.

As previously stated, existing competing technologies for dealing with stranded natural gas include hauling the flare gas by truck as CNG or LNG. These solutions are inferior to the MENG because of the logistical complexity and cost of transporting CNG and LNG compared to transporting a room temperature liquid such as methanol produced on site by the MENG. Alternatively, methanol today is currently produced in massive stationary industrial scale chemical plants, which must be supplied with pipeline natural gas or coal, which are commercial feedstocks that cost money, as opposed to flare gas, which is free. Furthermore, making methanol out of such marketable fuels does nothing to reduce flaring or $CO_2$ emissions. Systems that make methanol out of flare gas have frequently been proposed, but such systems require steam and oxygen, making their product expensive. MENG does not use either steam or oxygen, drastically reducing the cost of methanol production. Thus, the MENG is uniquely advantageous. By using the MENG, the over 120 billion cubic feet per year that was flared in North Dakota in 2014 could be converted into over 6 million tons of methanol.

Accordingly, one embodiment of the present invention is a mobile system for converting raw natural gas into methanol, comprising a syngas generator for generating syngas from the raw natural gas and air; a syngas compressor for compressing the syngas; a reactor for converting carbon monoxide and hydrogen in the syngas to methanol; and a power generator for using unreacted carbon monoxide and hydrogen to generate power, wherein some of the power is used to power the syngas compressor.

Another embodiment of the present invention is a method for converting raw natural gas into methanol using air as a source of oxygen, comprising a syngas generation step for generating syngas from the raw natural gas and the air in an air reforming unit, wherein the syngas comprises carbon monoxide, hydrogen, and nitrogen; a syngas compression step for compressing the syngas that comprises the carbon monoxide, the hydrogen, and the nitrogen; a methanol synthesis step for synthesizing methanol from the syngas over a catalyst bed; and a power generation step for using unreacted carbon monoxide and hydrogen in the syngas to generate power, wherein some of the power is used to power the syngas compression step, and wherein unreacted nitrogen is returned to atmosphere.

In some embodiments of the present invention, first sulfur is removed from the raw natural gas.

In some embodiments of the present invention, the syngas generation step comprises reforming the raw natural gas and the air in a presence of a steam reforming catalyst.

In some embodiments of the present invention, air enriched in oxygen is used to increase concentrations of hydrogen and carbon monoxide in the syngas.

In some embodiments of the present invention, water is added to the air reforming unit to prevent catalyst coking.

In some embodiments of the present invention, the water is recycled to the air reforming unit from a condenser downstream from an air recycling unit.

In some embodiments of the present invention, the water is converted to steam inside the air reforming unit.

In some embodiments of the present invention, a gas mixer mixes the raw natural gas and the air before these gases pass through a syngas catalyst bed in the air reforming unit.

In some embodiments of the present invention, the raw natural gas and the air are preheated to improve carbon monoxide yield.

In some embodiments of the present invention, the catalyst bed comprises a syngas-to-methanol synthesis catalyst.

In some embodiments of the present invention, the syngas-to-methanol synthesis catalyst comprises Cu—ZnO.

In some embodiments of the present invention, the methanol is removed from an effluent of the catalyst bed.

In some embodiments of the present invention, a heat exchanger is used to cool effluent gases to a temperature at which most of methanol vapor condenses to liquid, a phase separator to separate liquid methanol from gases, and a component for draining liquid methanol.

In some embodiments of the present invention, the syngas is preheated before the catalyst bed.

In some embodiments of the present invention, energy is exchanged between streams entering and exiting the catalyst bed to reduce duties on syngas preheating and syngas cooling.

In some embodiments of the present invention, energy released in the methanol synthesis step is removed from the catalyst bed.

In some embodiments of the present invention, carbon monoxide conversion to methanol is enhanced by using a recycle blower.

In some embodiments of the present invention, carbon monoxide conversion to methanol is enhanced by using cascading catalyst beds with methanol being removed between the cascading catalyst beds.

In some embodiments of the present invention, the power is generated by combusting the unreacted carbon monoxide and hydrogen in a spark ignited internal combustion engine, and using engine power to drive an electric generator.

In some embodiments of the present invention, some of the syngas is recirculated back to the syngas generating step to prevent hot spots in the catalyst bed.

In some embodiments of the present invention, the syngas generation step utilizes a pressure range of 0.1 and 10 bar.

In some embodiments of the present invention, a temperature of the syngas generation step is between 400 to 1000° C. (673-1273 K).

In some embodiments of the present invention, a temperature of the syngas generation step is above 700° C. (973 K).

In some embodiments of the present invention, the syngas compression step compresses the syngas to about 600 psi (41 bar).

In some embodiments of the present invention, the methanol synthesis step utilizes a pressure range of 10 and 1,000 bar.

In some embodiments of the present invention, a temperature of the methanol synthesis step at an inlet of the catalyst bed is between 170 and 250° C. (443-523 K).

In some embodiments of the present invention, the air reforming unit operates at a high-temperature but low pressure, whereas the methanol synthesis step operates at high pressure but low temperature. That is, the part of the system that is high-temperature is at a low pressure that does not challenge steel, and the part of the system that is high-pressure is at a low temperature that similarly does not challenge steel. This allows for a compact and portable design for a system designed for field deployment in a mobile unit.

Other features, utilities, and advantages of the various embodiments of the invention will be apparent from the following more particular description of various embodiments of the present invention.

BRIEF DESCRIPTION OF THE DRAWINGS

The invention will be understood by the following detailed description in conjunction with the accompanying drawings, wherein like reference numerals designate like structural elements, in which:

FIGS. 1, 1A, 1B, and 1C show a block diagram of one embodiment of a MEthanol from Natural Gas ("MENG") system.

FIG. 8 illustrates an example use case of the MENG in which a portion of the methanol stream is used directly in methanol-capable vehicles and/or transported as a liquid fuel.

DETAILED DESCRIPTION OF THE INVENTION

Figure 1A:
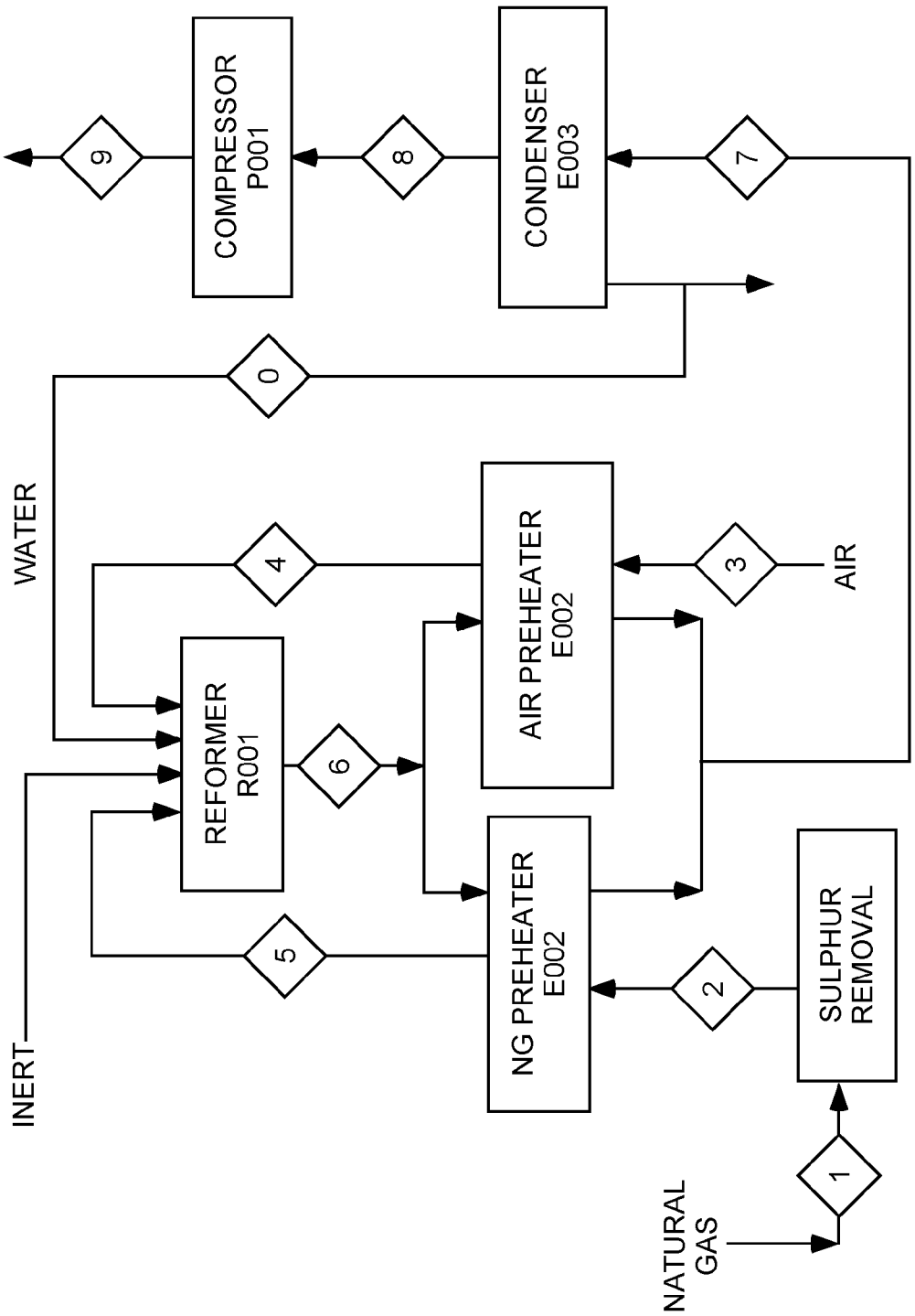

The following description is merely exemplary in nature and is in no way intended to limit the scope of the present disclosure, application, or uses.

Definitions

The following terms of art are provided for illustrative and explanatory purposes only, and are not intended to limit the application, intended uses, or scope of the present invention.

Throughout this disclosure "MENG-170," "full scale" apparatus, or any reference to a single full-scale module, will refer to an apparatus module that can process about 170 mcf (thousand cubic feet) of raw natural gas per day. Multiple modules can be combined for higher gas flow rates. These product flow estimates are provided for explanation purposes only, and are not intended to be limiting the scope of the present invention in any way. Different input raw gas compositions would produce different quantities of products.

The symbols cf, CF, scf, and SCF shall all stand for standard cubic feet ($ft^3$). The symbols mcf, MCF, and kcf will all stand for a thousand standard cubic feet (1,000 scf). The symbols MMCF, MMcf, and mmcf will all stand for a million standard cubic feet (1,000,000 scf or 1,000 mcf). The word "day" shall mean "a day of operations," which shall be a 24-hour day, but could also be an 8-hour day, a 12-hour day, or some other amount of operational time. 1 scf=0.02832 standard $m^3$=28.32 L.

Natural gas at the wellhead is commonly a mixture of methane (C1) with other hydrocarbons, including ethane (C2), propane (C3), butane (C4), pentane (C5), and hexane and higher (C6+). Wellhead natural gas also contains other compounds such as water vapor ($H_2O$), hydrogen sulfide ($H_2S$), carbon dioxide ($CO_2$), oxygen ($O_2$), and nitrogen ($N_2$). Also known as raw natural gas. Pure methane is also included within this definition.

Associated gas is natural gas produced as a by-product of oil drilling, either conventional or unconventional extraction (such as hydraulic fracking for tight oil). Also known as raw natural gas.

Flare gas is natural gas, usually associated gas, that is flared (burned for no useful purpose) because natural gas pipelines are not in place when the oil well is drilled. Also known as raw natural gas.

Stranded gas is natural gas, usually associated gas that is flared, that cannot be brought to market either because it is off-shore or too far from natural gas pipelines/infrastructure. Also known as raw natural gas.

As used herein, the phrase raw natural gas, or even more simply natural gas, shall be interchangeable with, and could mean, all the following: unprocessed natural gas, associated gas, flare gas, and/or stranded gas, and is meant to encompass all such raw natural gas sources.

Wet gas is natural gas that contains a high proportion of C2+ components (typically more than 10%). Wet gas is frequently also saturated with water vapor. This is an approximate definition often used by those skilled in the art.

Dry gas is natural gas with typically less than 5% C3+ components, or typically less than 10% C2+ components. This is an approximate definition often used by those skilled in the art.

Natural gas liquids (NGLs) are C3+ components, including propane and heavier hydrocarbons, and may include small amounts of methane and ethane. Other definitions sometimes include ethane as an NGL (natural gas liquid).

LPG is an acronym for Liquefied Petroleum Gas, which is generally a term for pressurized, processed gas mixtures of C3+ components, most commonly primarily propane and butane.

CNG is an acronym for Compressed Natural Gas, which is typically mostly methane (C1) compressed to a pressure above approximately 140 bar/2,000 psig, although higher or lower pressures are also possible.

LNG is an acronym for Liquefied Natural Gas, which is typically mostly methane (C1) at a pressure and a temperature in which it is a liquid phase.

Methanol, or MeOH, is the simplest alcohol, and a potential gasoline blendstock/substitute.

Overview of the MENG System

It is highly disadvantageous—both from a financial and an environmental perspective—to flare natural gas that could be sold for a profit. It is even more disadvantageous to spend large amounts of money on liquid fuel for vehicle fleets, and at the same time flare methane that could be doing the same job. The problem is that raw natural gas cannot be used in automotive engines and cannot be transported by truck. The inventors recognized that what is needed is a mobile system that can go to a well-site that is currently flaring gas, and process the raw natural gas into a liquid fuel—methanol—that can be used for transportation, to generate power, or for other purposes, and/or that can be transported for sale. It is to meet this unmet need that the inventors have developed the MEthanol from Natural Gas (MENG) system.

The MENG is a truck-mobile methane-to-methanol conversion system scaled to meet local needs. The MENG system can use any kind of natural gas, wet or dry, as its feedstock, to produce methanol, which is a viable gasoline substitute fuel without refining. In what follows, it is assumed that the feedstock is pure methane. The presence of higher hydrocarbons in the gas increases the yield in proportion that the total amount of carbon in the gas is increased. The system works using industrial catalysts—no expensive precious metal catalysts are needed. First, the methane is reformed at ~1 bar using preheated air over Ni catalyst to produce hydrogen and carbon monoxide. The resulting gas is then compressed to ~40 bar and then reacted in a Cu—ZnO catalyst bed to produce methanol. The system is simple enough overall to enable implementation in a compact field-mobile form. From 170 mcf/day of flare gas, the system can produce about 4.8 tons/day of methanol. In short, the new methanol system can use waste flare gas or stranded natural gas, located anywhere in the world, and produce a valuable clean burning gasoline substitute fuel.

Process Overview and Chemistry: Methanol is produced from the low pressure catalytic partial air oxidation of natural gas to syngas (CO and $H_2$) at one bar. The syngas is then compressed to 40 bar, and fed into a single-step methanol synthesis reactor using methanol synthesis catalyst. The methanol vapor at the synthesis reactor outlet is condensed to liquid methanol at ambient temperature. The principal reactions for the MENG are given in reactions (1)-(3):

Syngas Generation:

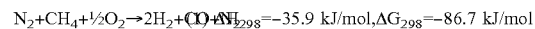
$$N_2+CH_4+\tfrac{1}{2}O_2\rightarrow 2H_2+CO+N_2 \quad \Delta H_{298}=-35.9 \text{ kJ/mol}, \Delta G_{298}=-86.7 \text{ kJ/mol}$$

Methanol Synthesis:

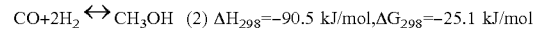
$$CO+2H_2 \leftrightarrow CH_3OH \quad (2) \quad \Delta H_{298}=-90.5 \text{ kJ/mol}, \Delta G_{298}=-25.1 \text{ kJ/mol}$$

Net Reaction:

$$CH_4 + \tfrac{1}{2}O_2 \rightarrow CH_3OH \quad (3) \quad \Delta H_{298} = -126.4 \text{ kJ/mol}, \Delta G_{298} = -111.8 \text{ kJ/mol}$$

Process Flow Diagram: A preliminary process flow diagram and stream summary for the MENG process is shown in FIG. 1 (1A-1C) and Tables 1 and 2, in which 4840 kg/day of high purity methanol product is generated from a starting flow rate of 8400 SLPM air and 3300 SLPM of methane.

The MENG contains three main process sub-systems: (1) Syngas Generation, (2) Syngas Compression, and (3) Methanol Synthesis, which are shown in FIG. 1 and discussed in turn below. Flow rates of inputs and products for this embodiment are shown in Table 1.

TABLE 1

MENG System Flow Rates

| | |
|---|---|
| Methane feed rate | 3300 L/min = 2.4 kg/min = 170 mcf/day |
| Air feed rate | 8400 L/min |
| Methanol Production Rate | 202 kg/hour = 4840 kg/day = 6900 gal/day (@ 25° C.) |
| Power requirement | 180 kWe |
| Value of methanol product | ~$3,000/day |

Figure 2:
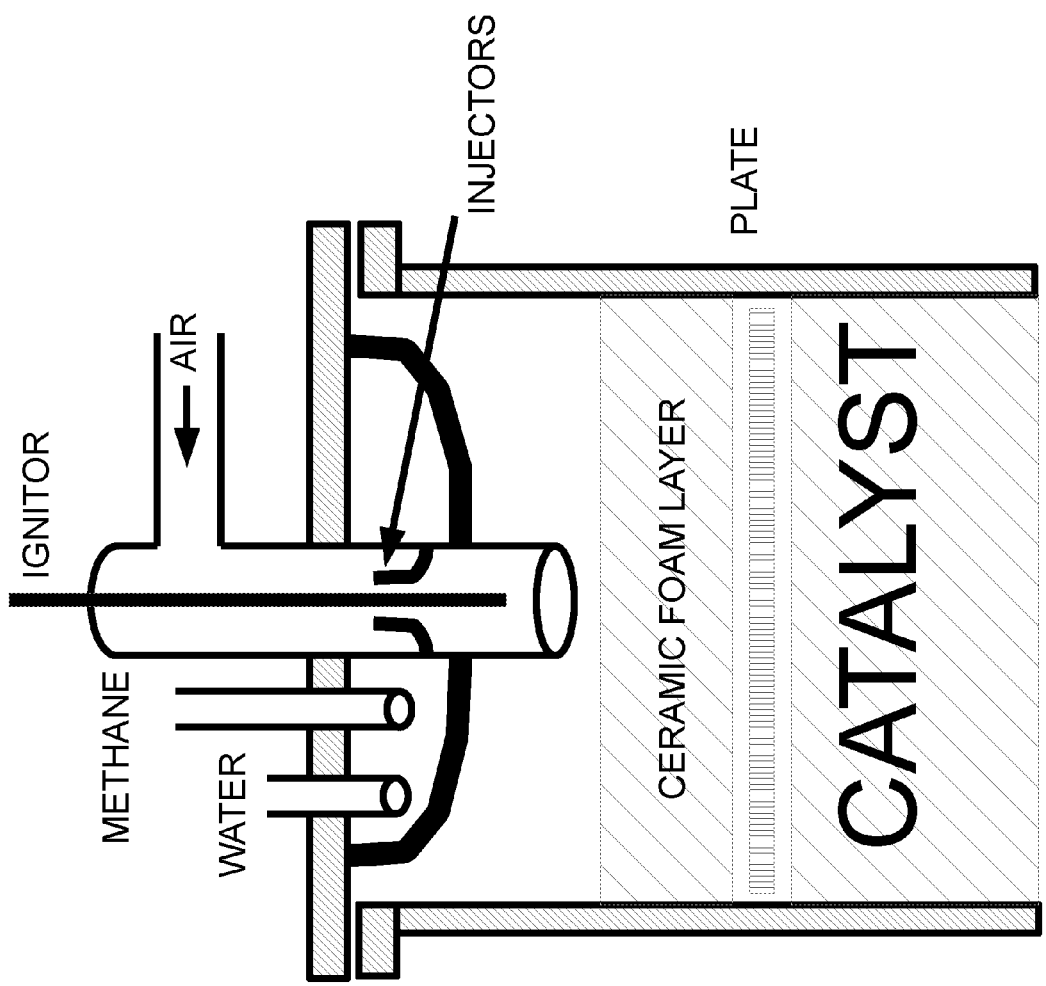
FIG. 2 shows a schematic of one embodiment of an air reforming unit according to one embodiment of the present invention.

Syngas Generation: As shown in FIG. 1A, to prevent downstream catalyst poisoning, the natural gas (Stream 1) is preconditioned with a desulfurization catalyst to reduce background sulfur concentration below 1 ppmv. The reactant gases methane (Stream 2) and air (Stream 3) are then preheated to 600 K before entering the Syngas Generator (Streams 4 and 5). This is accomplished by using gas heat exchangers and the excess heat from the syngas exiting the Syngas Generator (Stream 6). The Syngas Generator is operated at pressure close to ambient pressure and temperature range 970-1170 K, and at these conditions a stream with a $H_2$/CO mole ratio of approximately 2:1 is generated from the reactor. FIG. 2 shows a schematic of one embodiment of an air reforming unit useable for syngas generation in some embodiments of the present invention which is described in greater detail below.

Syngas Compression: Syngas from Syngas Generator (Stream 7) is cooled to 308 K, compressed to 40 bar with a four-stage compressor in Stream 9, and then sent to the Methanol Generator.

Methanol Synthesis: Conversion of CO to methanol is limited by equilibrium for the reaction (2). To alleviate this limit imposed by thermodynamics, the product (methanol) of the synthesis reaction (2) is removed to force the reaction (2) forward. This is implemented using either the recycle scheme or cascading reactors scheme illustrated on FIGS. 1B and 1C, respectively. In the recycling scheme, the syngas is recirculated by the recycle blower P002 through the catalyst bed to achieve acceptable CO conversion. Before syngas reaches the catalyst bed, stream 9 is preheated using heat recovery heat exchanger E005 and reactor preheater E004. Heat recovery heat exchanger E005 is used to reduce duties on the heat exchangers E004 and E006. The temperature of the syngas at the inlet of the catalyst bed is in the range 473-523 K. After reasonably close approach to equilibrium in reaction (2) is achieved in catalyst bed R002, the methanol product is removed. This is achieved by cooling stream 13 using heat recovery heat exchanger E005 and cooler E006 to temperatures below 298 K for stream 15. At these temperatures, methanol condenses and is separated by the gas using phase separator S001. Liquid methanol is drained as stream 18. Stream 16 after the phase separator S001 is split into two streams. One of the streams, stream 19, is vented to prevent buildup of nitrogen in the methanol generator. The other stream is recirculated into catalyst bed using recycle blower P002. Typical recycle ratios for this scheme are in the range of 3 to 6.

Figure 1B:
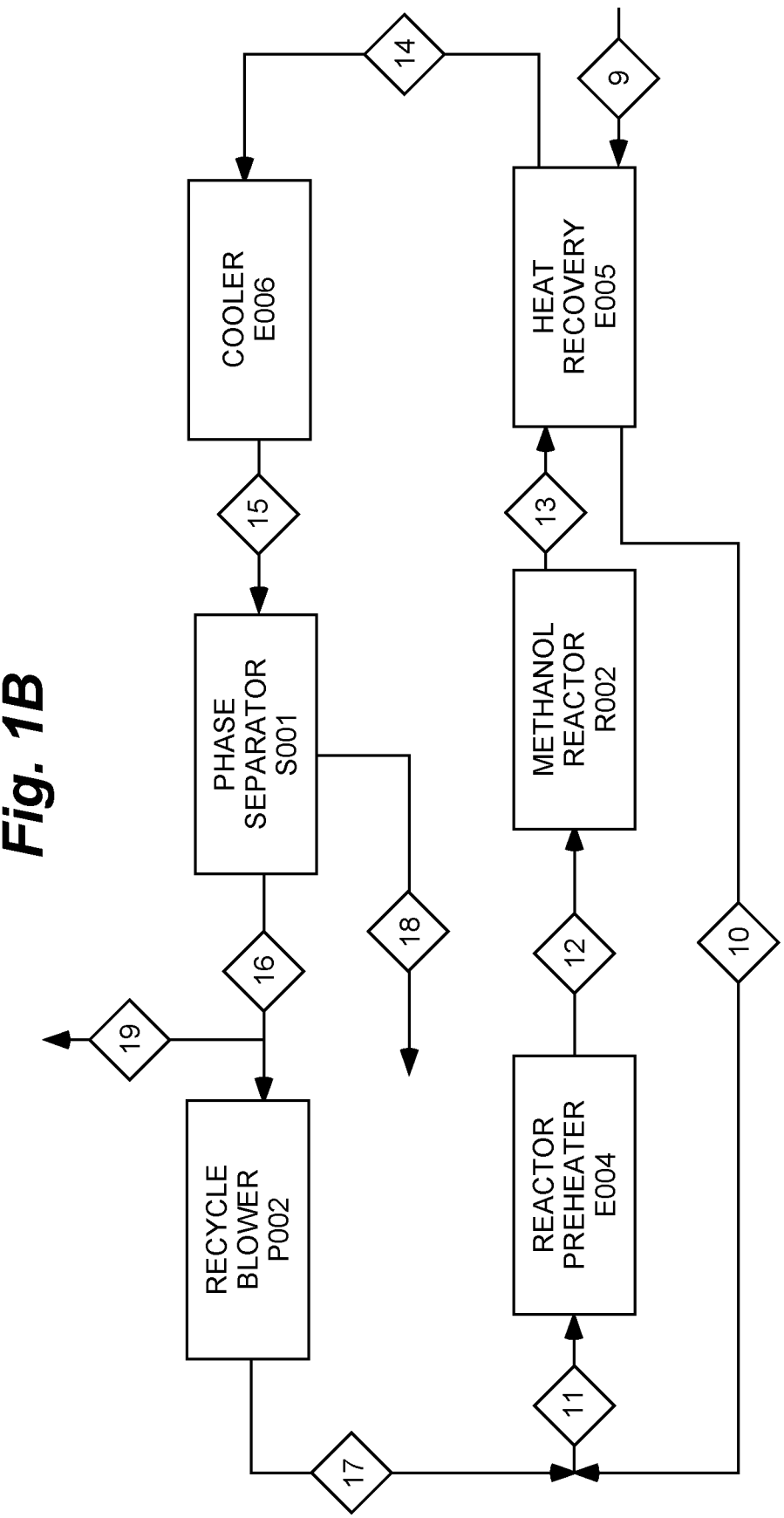
Figure 1C:
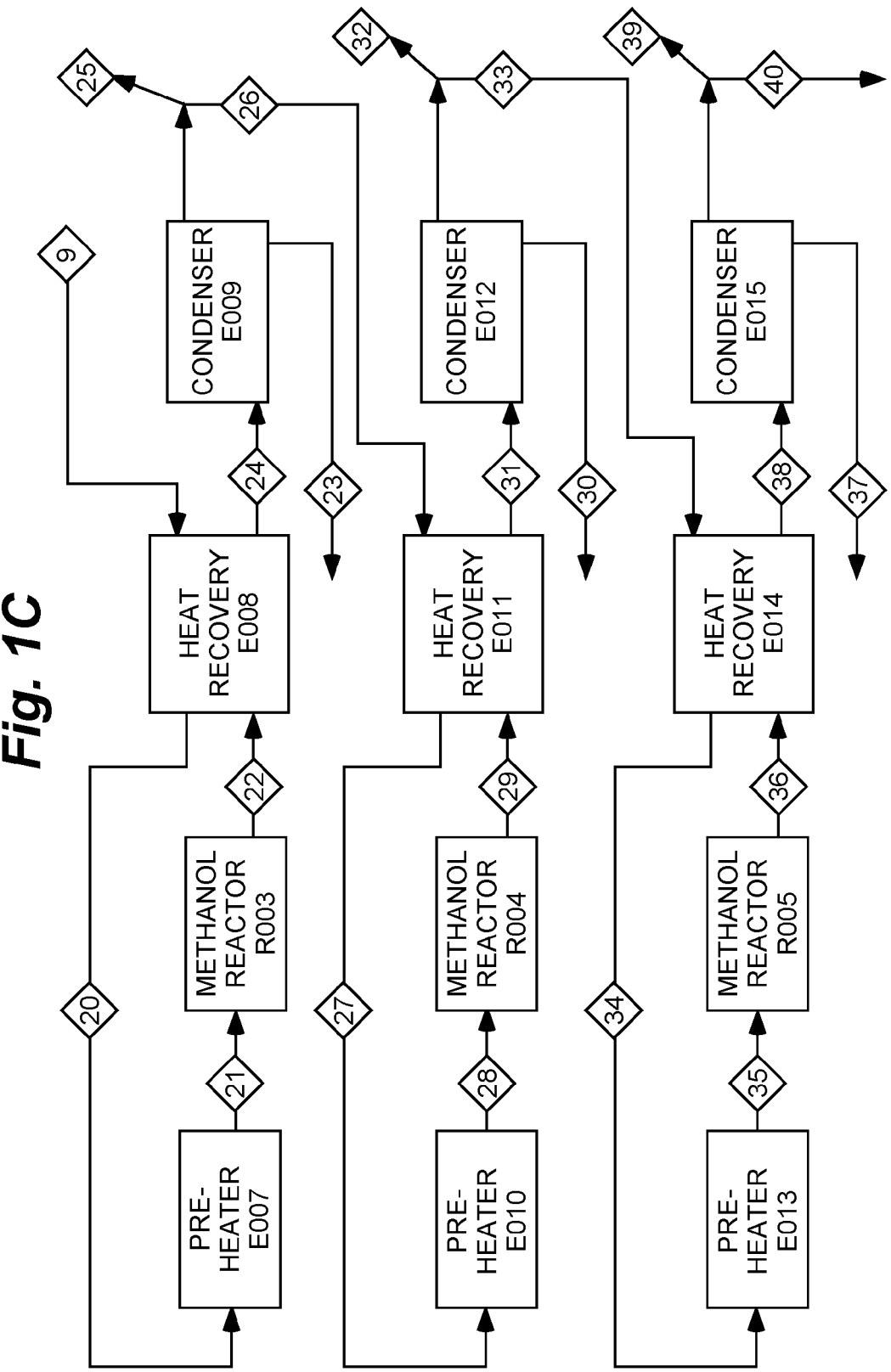

The cascading reactor scheme illustrated on FIG. 1C is conceptually similar to the recycle scheme illustrated on FIG. 1B. In the cascading reactor scheme, after the syngas is passed through the catalyst bed R003, the methanol product is removed in condenser E009 so that more methanol can be made in the next catalyst bed R004. For 40% CO conversion in each reactor, total conversion of 78% is achieved using three reactors. Using only two reactors with 40% conversion in each reactor, total conversion of 64% is achieved, which is acceptable. The advantage of this scheme is that no recycle blower is required, and separate catalyst beds can be operated at different temperatures to optimize methanol conversion.

A stream summary is presented in Table 2 that summarizes the key process points for the system.

TABLE 2

Simplified Process Stream Table for Key Stream Points

| | unit | Stream 0 | Stream 5 | Stream 4 | Stream 6 | Stream 8 | Stream 9 |
|---|---|---|---|---|---|---|---|
| Temperature | K | 298 | 873 | 873 | 1023.424 | 313 | 525.962 |
| Pressure | bar | 1 | 1 | 1 | 1 | 1 | 40 |
| Mole fract.: | | | | | | | |
| $O_2$ | | 0 | 0 | 0.33 | 0 | 0 | 0 |
| $N_2$ | | 0 | 0 | 0.67 | 0.24488 | 0.246801 | 0.261856 |
| $CH_4$ | | 0 | 1 | 0 | 0.011983 | 0.012077 | 0.012813 |
| CO | | 0 | 0 | 0 | 0.222244 | 0.223987 | 0.237651 |
| $CO_2$ | | 0 | 0 | 0 | 0.004745 | 0.004783 | 0.005074 |
| $H_2$ | | 0 | 0 | 0 | 0.444488 | 0.447974 | 0.475301 |
| $H_2O$ | | 1 | 0 | 0 | 0.071659 | 0.064378 | 0.007305 |
| $CH_3OH$ | | 0 | 0 | 0 | 0 | 0 | 0 |
| Overall flow | mol/s | 0.215 | 0.826447 | 1.264 | 3.458341 | 3.431426 | 3.234142 |
| Overall MW | kg/mol | 0.018015 | 0.016043 | 0.029329 | 0.015673 | 0.015655 | 0.015511 |
| Mass flow | kg/s | 0.003873 | 0.013259 | 0.037072 | 0.054203 | 0.053718 | 0.050164 |

TABLE 2-continued

Simplified Process Stream Table for Key Stream Points

| | unit | Stream 12 | 13 | 16 | 18 | 19 | 17 |
|---|---|---|---|---|---|---|---|
| Temperature | K | 493 | 513 | 333 | 333 | 333 | 333 |
| Pressure | bar | 40 | 40 | 40 | 40 | 40 | 40 |
| Mole fract.: | | | | | | | |
| $O_2$ | | 0 | 0 | 0 | 0 | 0 | 0 |
| $N_2$ | | 0.447441 | 0.508628 | 0.544475 | 0.008078 | 0.544475 | 0.544475 |
| $CH_4$ | | 0.021806 | 0.024788 | 0.026508 | 0.000772 | 0.026508 | 0.026508 |
| CO | | 0.16708 | 0.121554 | 0.130183 | 0.00106 | 0.130183 | 0.130183 |
| $CO_2$ | | 0.008275 | 0.009406 | 0.009948 | 0.001843 | 0.009948 | 0.009948 |
| $H_2$ | | 0.334316 | 0.243286 | 0.260603 | 0.001475 | 0.260603 | 0.260603 |
| $H_2O$ | | 0.002769 | 0.003147 | 0.000397 | 0.04155 | 0.000397 | 0.000397 |
| $CH_3OH$ | | 0.018313 | 0.089191 | 0.027887 | 0.945223 | 0.027887 | 0.027887 |
| Overall flow | mol/s | 9.418974 | 8.285894 | 7.732163 | 0.553732 | 1.546433 | 6.18573 |
| Overall MW | kg/mol | 0.019239 | 0.02187 | 0.021188 | 0.031388 | 0.021188 | 0.021188 |
| Mass flow | kg/s | 0.181213 | 0.181213 | 0.163833 | 0.01738 | 0.032767 | 0.131066 |

Catalysts and Operating Conditions

Various catalysts may be used in reforming and hydrogenation reactions of the invention. The catalyst used may contain one or more transition metal such as ruthenium, palladium, platinum, rhodium, nickel, iridium, rhenium, copper, zinc, chromium, nickel, iron, cobalt, or combinations of thereof. The catalyst may contain a combination of one or more transition metals with main group elements, such as, for example, platinum and tin, or ruthenium and tin. The catalyst may contain promoters such as barium hydroxide, magnesium hydroxide, and so on. Reduction or hydrogenation may also be done using Raney type sponge catalysts, such as Raney nickel, copper, cobalt, and so on, optionally bearing promoters, such as iron, molybdenum, chromium, palladium, and so on.

Catalysts used in reductions may be supported or unsupported. A supported catalyst is one in which the active metal(s) are deposited on a support material, e.g., by soaking or wetting the support material with a metal solution, spraying or physical mixing followed by drying, calcination, and finally reduction with hydrogen if necessary to produce the active catalyst. Catalyst support materials used frequently are porous solids with high surface areas, such as silica, alumina, titania, magnesia, carbon, zirconia, zeolites, and so on.

The reforming step may be run under different temperature and pressure conditions to achieve acceptable conversions. Pressures may range between ~0.1 and ~10 bar, or preferably between ~0.5 and ~1 bar. Temperatures for the reforming step may be in the range of ~400 to ~1000° C., preferably between ~500 and ~900° C., and more preferably at about 700° C. The Weight Hourly Space Velocity (WHSV) may be around $7500^{-h}$.

The methanol synthesis step may be run at pressures between ~10 and ~1000 bar, preferably between ~20 and ~60 bar, and around ~40 bar in some embodiments. Temperatures for the methanol synthesis step may be between ~170 and ~250° C., or about 220-230° C. in some embodiments. The WHSV may be about $1500^{-h}$.

Pilot Unit Description

The inventors have built and tested several embodiments of the present invention. These sections present various experimental results from such tests.

A pilot unit was built to demonstrate MENG on a substantial scale. The unit was run with the methane feed rate up to 500 SLM, or 18 SCFM. CO yields in excess of 84% from the air reforming unit were demonstrated. With 70% yield of methanol from syngas, the pilot unit would produce approximately 600 kg of methanol per day.

A schematic of the air reforming unit is shown in FIG. 2. Air enters the reformer unit from the top through a 3-inch air supply pipe. The air supply pipe is concentric with the flange on a top of the reformer. A plenum is constructed by welding a pipe cap to the flange in a concentric arrangement. Natural gas enters the plenum and then injected into the air supply pipe using injectors. Injectors direct velocity of the natural gas flow to provide two velocity components. One velocity component of the natural gas stream is collinear and opposite to the velocity of the air stream. The other velocity component is perpendicular to the velocity of the air stream and generates a swirl to improve mixing.

The water stream enters a plenum where water is vaporized on contact with hot metal. The resulting steam is injected alongside with the natural gas.

An igniter is used to ignite a gas mixture to preheat the reformer.

A layer of the ceramic foam is placed on top of the catalyst to protect catalyst from a thermal shock during reformer preheating. A perforated plate is placed on top of the catalyst bed to separate ceramic foam layer from the catalyst pellets.

The syngas stream from the reformer contains a significant amount of water vapor. This water vapor comes from the water added to the reforming process as well as from the reactions between methane and air. Before compressing the reformer gas in a compressor, the majority of the water vapor is removed in a condenser. The pilot unit condenser is of a single pass tube side and single pass shell side construction. Cooling water is on a shell side and the syngas is on a tube side. The tube bundle was constructed from approximately 250 tubes of 0.375-inch diameter; each tube is 5 feet long.

The compressor is a four-stage compressor with interstage cooling. The compressor can compress a flow of 6000 standard liters per minute (SLM) of reformer gas to a pressure of 600 psia, or approximately 40 bara. The compressor is driven by two electrical motor with a total power rating of 80 HP (107 kW). The compressor is capable of handling of 5× turndown.

After the compressor, the syngas is directed into the synthesis reactor detailed on FIG. 1. Before entering the reactor, the syngas (stream 9) is preheated in a gas preheater to a temperature above 200° C. The preheated syngas, stream 10, enters the synthesis reactor. In the pilot unit, the shell of the synthesis reactor is constructed from a 6-inch diameter heavy wall pipe, which is approximately 5 feet long. The top end of the reactor was flanged using a raised face gasketed flange rated at 800 pounds and the bottom end of the reactor is capped using a pipe cap with the same 800-pound rating. To preheat the catalyst and to remove the energy from the reactor, the internal tube coils and external cooling jacket were integrated into the reactor. The external cooling jacket was constructed from an 8-inch diameter pipe and a couple of rings. The heat transfer fluid is circulated in an annular space between the 6-inch pipe and 8-inch pipe. The temperature and the flow rate of the heat transfer fluid are controlled by a separate subsystem. This subsystem contains a recirculation pump with a variable frequency drive, a system for measuring a flow rate of heat transfer fluid, a reservoir tank with inert gas purge, an expansion tank and the cooling/heating elements.

Process Flow Chart

Figure 3:
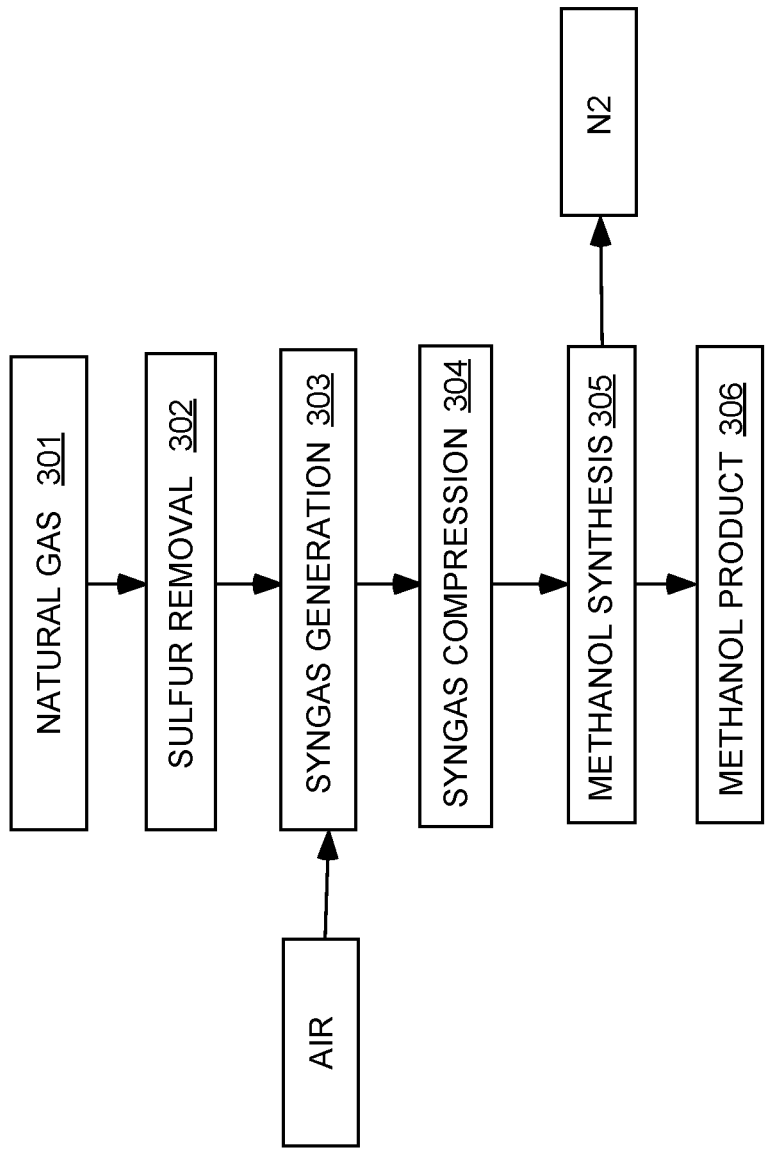
FIG. 3 shows a flowchart of a process for producing methanol from flare gas according to one embodiment of the present invention.

FIG. 3 shows a flowchart of a process for producing methanol from raw natural gas according to one embodiment of the present invention. An embodiment of the present invention is a method for converting natural gas 301 into methanol 306 as shown. First, any sulfur is removed from the raw natural gas stream as it may poison catalysts, as shown in step 302. Then syngas is generated from the desulfurized natural gas and air, as shown in step 303. The syngas is compressed utilizing a compressor, as shown in step 304. The compressed syngas is converted into methanol in the methanol synthesis step, as shown in step 305. Unreacted nitrogen is returned to the atmosphere. The methanol product is removed at step 306.

Performance of Pilot Unit Reformer with Air

Figure 4:
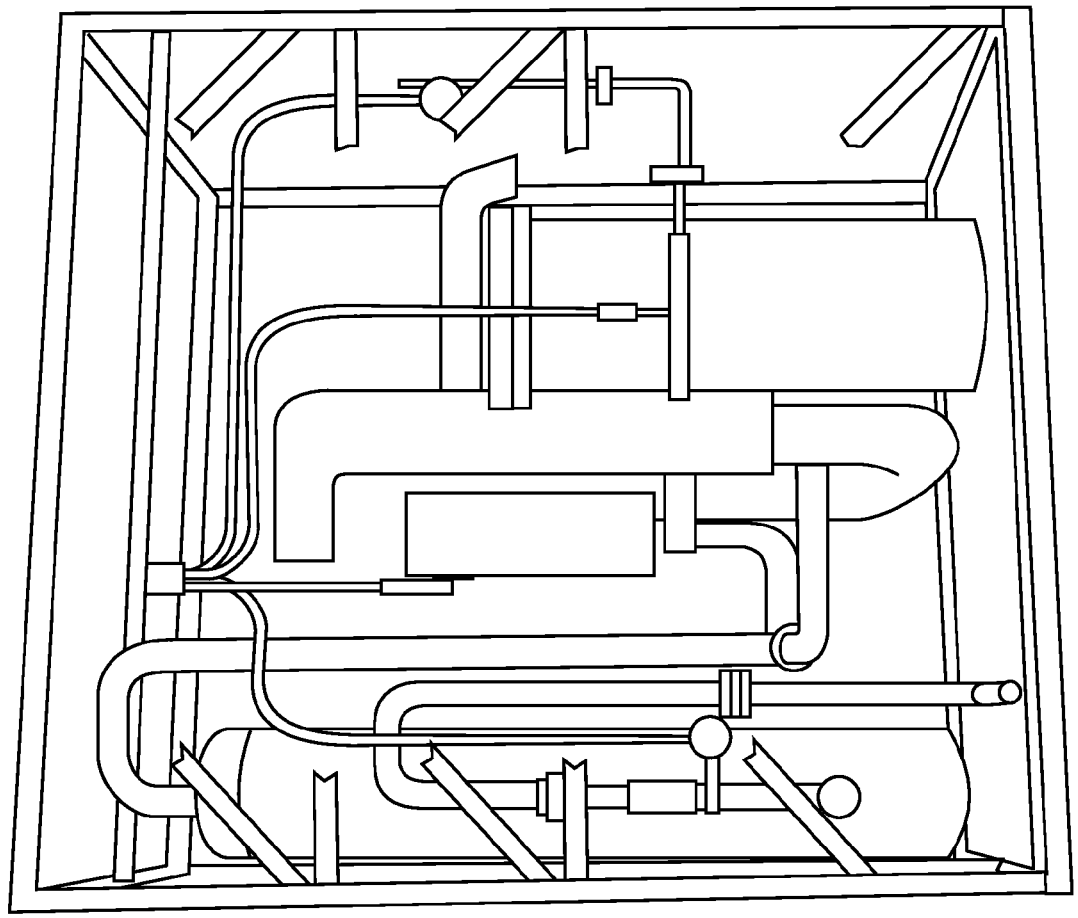
FIG. 4 shows a perspective view of a pilot MENG unit, according to just one embodiment of the present invention.

FIG. 4 illustrates a perspective view of a portion of the MENG pilot unit, according to one embodiment of the present invention.

To evaluate performance of the reformer, some meaningful quantitative metrics are needed. Carbon monoxide yield from methane is one such metric, and 100% conversion of methane to carbon monoxide would represent ideal operation of the reformer. However, 100% conversion of methane to carbon monoxide is not feasible, since some of the methane will be combusted to raise the temperature of the incoming gases and hence will not be available to make carbon monoxide product via the reforming process. In addition, thermodynamic equilibrium may limit carbon monoxide yield from methane. To investigate this, a computer simulation was performed to establish the maximum possible carbon monoxide yield in the reformer. This yield can be compared to the experimentally measured yield to establish how well the reformer works. For comparison with the experiment, let's consider the following case when the incoming gases (air and methane) are preheated to 400° C., the exit temperature of the reformer is 750° C., the molar ratio of water flow rate to methane flow rate is 1:4, and the air to methane ratio is 3.0. With the assumption that the reaction in the reformer reaches equilibrium, the calculated carbon monoxide yield is 83%, with the following calculated composition of dry gases out of the reformer: Hydrogen: 35.8%, Carbon monoxide: 15.4%, Carbon dioxide: 2.9%, Methane: 0.2%, Nitrogen, argon: balance.

These calculated numbers can be directly compared with the experimental results. In one test, the air and methane were preheated to the temperatures close to 400° C., the molar ratio of water flow rate to methane flow rate was approximately 1:4, and the temperature of gas exiting the reformer was approximately 750° C., the same conditions for which simulation was done. The CO yield of 84% was measured and the following composition of dry gases out of the reformer was measured: Hydrogen: 32.7%, Carbon monoxide: 16.2%, Carbon dioxide: 1.8%, Methane: 1.24%, Nitrogen, argon: balance.

Figure 5:
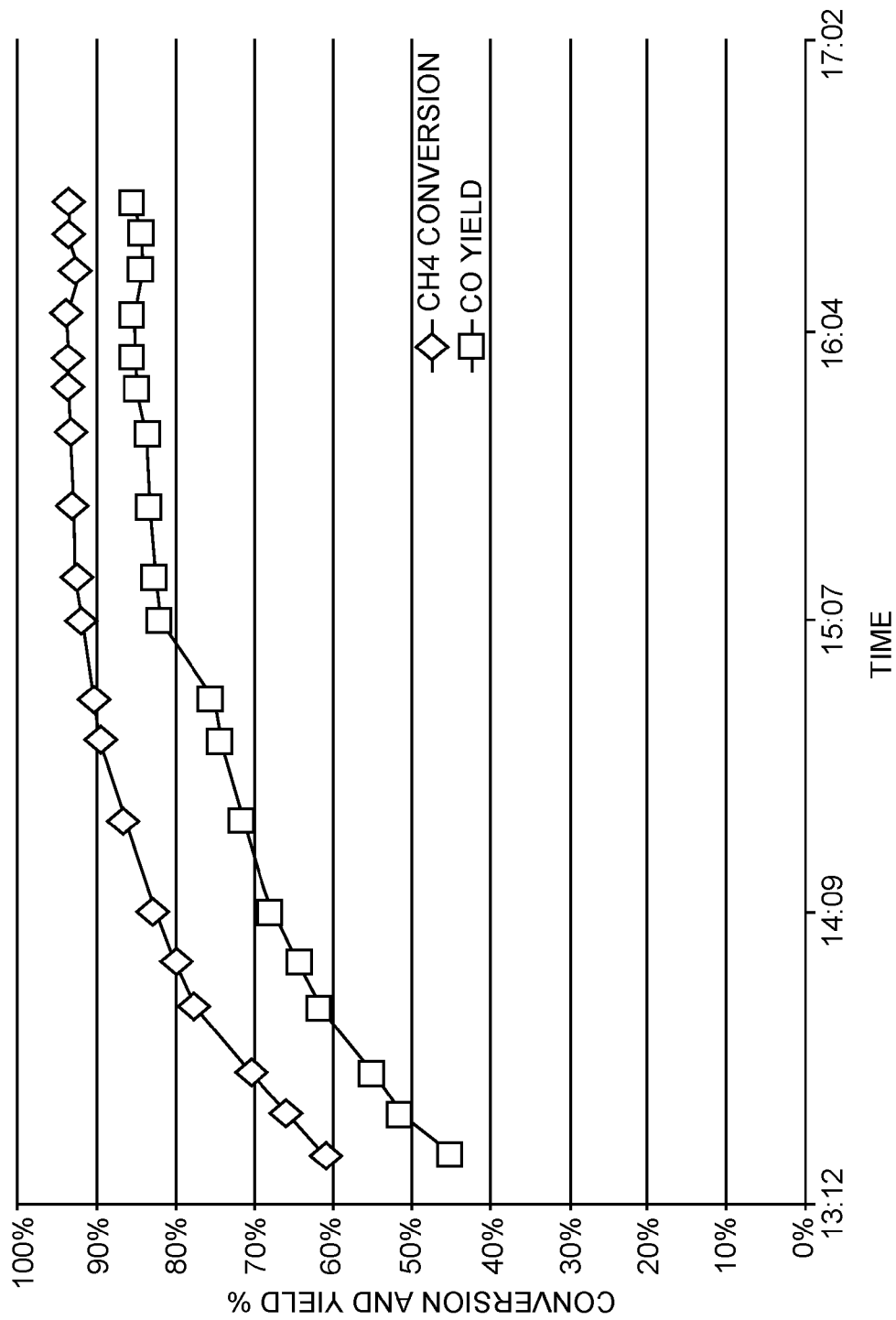
FIG. 5 illustrates a graph showing performance of a pilot air reforming unit with air, according to one embodiment of the present invention.

Calculated and measured results are remarkably close for space velocity corresponding to reforming of 300 SLM of methane with 900 SLM of air using 20 kg of catalyst, the conditions of the test. The time history of carbon monoxide yield and methane conversion along with some other relevant experimental data is shown in FIG. 5 for this representative test.

For preheating of methane and air streams, U-tube style heat exchangers were used. These heat exchangers were of 4 pass tube side and a single pass shell side construction. The inventors state that using true counter-flow heat exchangers with large surface area for gas preheating will improve performance of the reformer. Let's consider a case when air and methane are preheated to 700° C. instead of 400° C., while the exit temperature of the reformer is 750° C. Calculation shows that the CO yield improves to 94% and the dry gas composition from the reformer is as follows: Hydrogen: 39.4%, Carbon monoxide: 18.7%, Carbon dioxide: 0.8%, Methane: 0.03%, Nitrogen, argon: balance.

Calculation confirms than better reformer performance can be obtained when the gases are preheated to the maximum temperature which is the exit temperature of the reformer.

Performance of Pilot Unit Reformer with Oxygen-Enriched Air

Air contains approximately 20% oxygen with approximately 80% of nitrogen. The nitrogen component of air plays both positive and negative roles. On the positive side, nitrogen, being an inactive component with a significant heat capacity, moderate temperature extremes and reduces occurrences of hot spots. On the negative side, nitrogen dilutes carbon monoxide and hydrogen, reducing concentrations and partial pressures of these two gases. When partial pressures of hydrogen and carbon monoxide are decreased at the inlet of the methanol synthesis reactor, two things happen: 1) maximum possible conversion to products decreases because equilibrium shifts away from products; and 2) the absolute reaction rates decreases with the decreasing concentration of the reactants.

Operation of the reformer with oxygen-enriched air was demonstrated. On a smaller scale, a flow of 240 SLM air enriched to 33% oxygen was demonstrated by passing compressed air through a gas separation membrane. For a larger scale pilot unit reformer tests, oxygen enriched air was made by adding pure oxygen to the air stream. This was done because not enough gas separation membranes were available for the large-scale tests. In one test, the reformer was operated with air enriched to oxygen concentration 28.5%-30%. CO yield of 89% was achieved and the following composition of dry gas out of the reformer was measured: Hydrogen: 36%, Carbon monoxide: 21.3%, Carbon dioxide: 1.8%, Methane: 0.8%, Nitrogen, argon: balance.

In this test, water was added to the reformer at approximately 1:4 water to methane mole ratio to prevent catalyst coking. Catalyst temperature was 860° C. on top of the catalyst bed and 720° C. at the exhaust. The flow of methane was approximately 300 SLM and 20 kg of reforming catalyst was used for this test.

This test was simulated assuming equilibrium is achieved in the reformer and the following numbers were calculated. The conversion of methane to CO was calculated to be 93% which compares well to the experimental conversion of 90%. The dry gas composition out of the reformer was calculated to be: Hydrogen: 44.4%, Carbon monoxide: 22.2%, Carbon dioxide: 1.1%, Methane: 0.6%, Nitrogen: balance.

Figure 6:
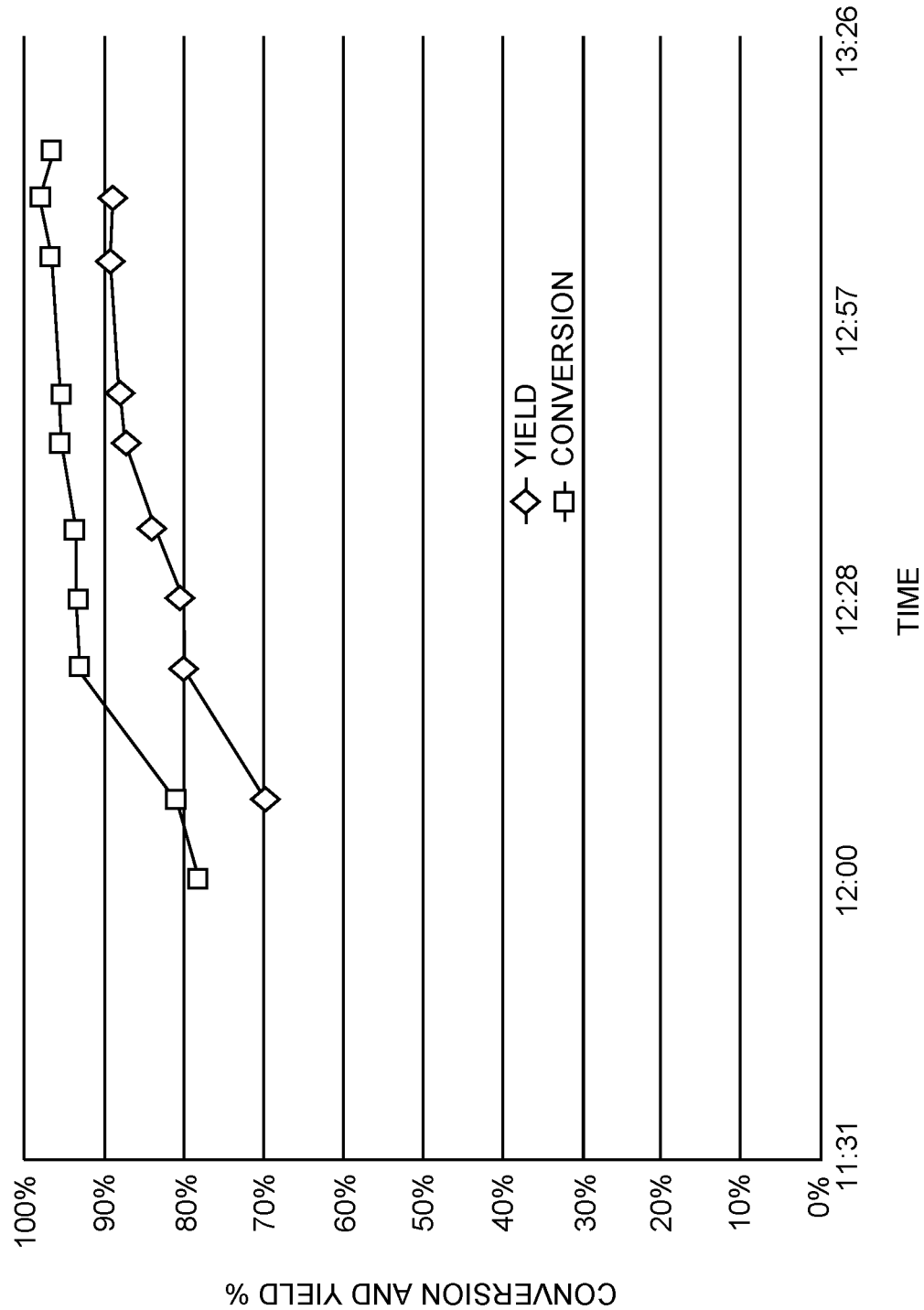
FIG. 6 illustrates a graph showing performance of the pilot air reforming unit with oxygen-enriched air.

As in the case with unenriched air, a good agreement between the calculated and experimental results is observed. This indicates good performance of the air reforming unit. The time history of CO yield and methane conversion along with some other relevant experimental data are shown in FIG. 6 (note symbols and legend for CO yield and methane conversion are reversed from the convention used in FIG. 5).

In another test, air enriched to approximately 40% oxygen was used. In this test, methane to water ratio was approximately 5:1, the reformer exhaust temperature was approximately 750° C. The following dry gas composition was measured: Hydrogen: 46%, Carbon monoxide: 23%, Carbon dioxide: 3.1%, Methane: 5.4%, Nitrogen: balance.

The syngas obtained in this test, with high CO concentration (23%), optimal hydrogen to carbon monoxide ratio of 2:1 and low inert gases concentration (31%) is well suited for synthesis of methanol.

Syngas Recirculation

In the experiment conducted with air enriched to 30% oxygen, high temperature (860° C.) near the top of the catalyst bed was observed. The manufacturer of the catalyst does not recommend exceeding 900° C. for the catalyst, which is why tests with air enriched to oxygen concentration higher than 30% were not attempted.

It is advantageous to use higher oxygen concentrations in enriched air to reduce nitrogen content in the syngas for improved methanol yield. However, without sufficient nitrogen gas entering the reformer, the hot spot near the top of the catalyst bed will develop, which results in damage to catalyst. The kinetics and thermodynamics of the reforming dictates that sufficient buffer gas needs to be present to prevent catalyst from overheating. As shown below, this buffer gas can be recirculated syngas.

Equilibrium in reforming of methane at low pressures and high temperatures favors formation of carbon monoxide and hydrogen products. If equilibrium is favorable, part of the syngas can be recirculated to the reformer. This was investigated by performing equilibrium calculation for the case of air enriched to 45% oxygen. Membrane separation can produce air enriched to 45% oxygen, and membrane separation is one of the methods of oxygen enrichment which is suitable for field deployment at remote locations.

In the equilibrium calculation for air enriched to 45% oxygen concentration, 35% of the syngas is recirculated back to the reformer. The recirculated syngas is split after the condenser because at this point the syngas is cold and can be recirculated using a blower, which does not have to withstand high temperatures. The enriched air feed and methane are assumed to be preheated to 400° C., and the ratio of methane to water is set to 4:1. The ratio of enriched air to methane is varied to obtain reformer exit temperature of 750° C. For these conditions, the following composition of dry gases at the exit of the reformer is obtained: Hydrogen: 50%, Carbon monoxide: 23%, Carbon dioxide: 4%, Methane: 0.5%, Nitrogen: 22.5%. These results show that significant reduction of nitrogen concentration in the syngas can be achieved if air enriched with oxygen and syngas recirculation is used. If the recirculated syngas is counted as nitrogen, the effective oxygen concentration in the feed is only 19%, which is low enough to prevent formation of hot spots.

The above example is for air enriched to 45% oxygen. The reformer can be operated with air enriched to oxygen concentrations other than 45%, provided that sufficient syngas is recirculated to prevent catalyst overheating while achieving high yield of carbon monoxide from methane.

Synthesis of Methanol from Syngas

Methanol synthesis was demonstrated in multiple tests. Conversion efficiency of CO to methanol varied with the reactor temperature, pressure, reformer gas composition, space velocity, reactor geometry, and other factors.

Figure 7:
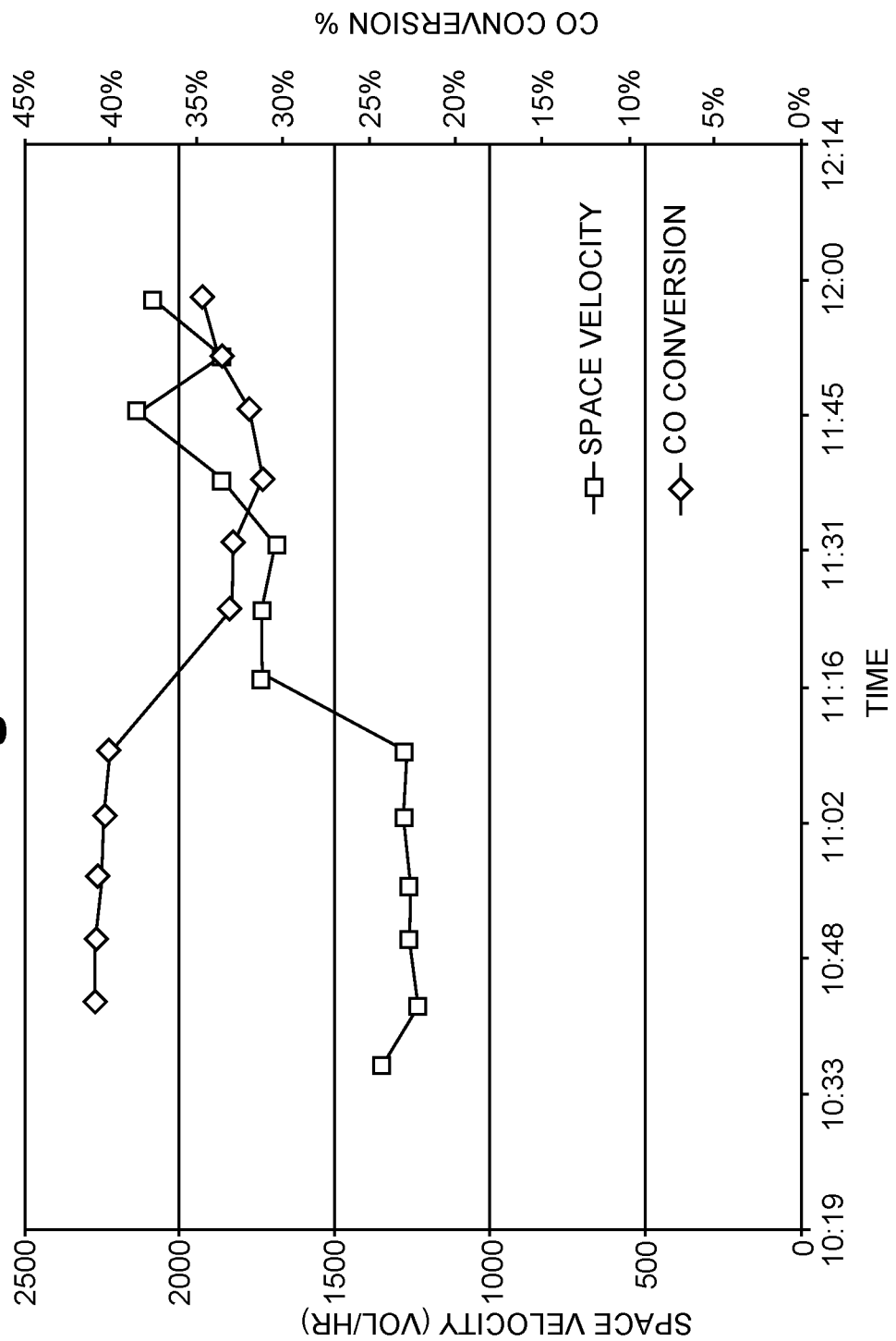
FIG. 7 illustrates a graph showing performance of the pilot MENG unit for methanol synthesis from syngas.

In one of the tests, the methanol reactor was a jacketed 1.75-inch (4.44 cm) diameter tube holding approximately 2 kg of CuO—ZnO catalyst. In the jacket, a heat transfer fluid (vegetable oil) was circulated to remove reaction energy. The syngas gas had the following composition: 23% CO, 45% $H_2$, and 32% $N_2$. Before entering the synthesis reactor, the reformer gas was preheated to a temperature of approximately 240° C. Catalyst temperature varied from 270° C. at the rector inlet to 220° C. at the reactor outlet. Conversion of approximately 40% were achieved at a space velocity of 1700 vol/hr and conversion of 32% was achieved at a space velocity of 2200 vol/hr. For pressure of 600 psia and stated reformer gas composition, equilibrium conversions of methanol are 40%, 48%, and 56% at temperatures 240° C., 230° C., and 220° C., respectively. The experimental results show that a close approach to equilibrium was achieved. After the run, 402 grams of liquid were collected. The GC analysis of the liquid showed that it was a high purity methanol with negligible amount of water and small amount of DME. Space velocity profile and conversion efficiencies are shown on FIG. 7.

Methanol Synthesis in the Pilot System Using Unenriched Air

Methanol synthesis in a pilot system was demonstrated. The reforming of methane was done using air at methane flow of 300 SLM and air flow approximately 900 SLM. Water to methane ratio was approximately 1:4. Methane conversion was 94% and CO yield was 78%. The following composition of dry gases out of the reformer was obtained: Hydrogen: 36%, Carbon monoxide: 16.4%, Carbon dioxide: 3.2%, Methane: 1.1%, Nitrogen, Argon: balance.

The reformer gas was compressed to 600 psia. Part of the compressed reformer gas was flared and a smaller part, approximately 200 SLM, was pre-heated and sent through the synthesis reactor. The following composition of dry gas at the outlet of synthesis reactor was measured: Hydrogen: 32.7%, Carbon monoxide: 11.8%, Carbon dioxide: 5.3%, Methane: 0.94%, Nitrogen, Argon: balance Approximately 1.4 kg of liquid were collected, which was analyzed using a GC. Analysis showed that the collected liquid was high purity methanol, with a water impurity less than 1% and DME impurity less than 2%. GC analyses and material balances are consisted with methanol yield of 30% on a single pass.

MENG System Advantages

The inventors are using catalysts which work adequately well in the presence of $N_2$. In the baseline approach, for syngas generation, the catalyst is a Ni-based steam reforming catalyst; for methanol synthesis, the catalyst is Cu—ZnO. The nitrogen (air) flow will influence the catalyst performance to the extent of lowering the partial pressures of the product constituents and increasing reactor size. This can be mitigated by oxygen enrichment of the air stream into the syngas generator. Some downstream benefits of oxygen enriched air (OEA) include reactant flow rate reduction, reduced air/NG preheater size (heat exchanger), enhanced partial pressure of CO and $H_2$, and lower pressure operation.

Since the MENG works without oxygen separation and without steam production, these are unique characteristics for this type of conversion. This makes the overall process simple, enabling the radical simplification necessary for field-deployment.

One key challenge is to avoid coking. Steam suppresses coking, but the inventors are doing this without steam. The inventors have found that if they can operate in a regime above 700° C., they can prevent coking. The challenge is to keep the reaction always above 700° C. Also, operating with air (without pure oxygen), they need effective heat exchange to pre-heat the air and methane—otherwise, the temperature does not get high enough. This is done in a one pass system to ensure simplicity. No oxygen production subsystems or steam boilers are needed.

Unlike a typical system that is high pressure and high temperature, the part of our system that is hot is operating near atmospheric pressure: the front half of the system is 800° C., but below 15 psi; in the part of the system that is high-pressure (300 psi), the temperatures are below 250° C., which does not challenge steel.

In short, the system and process are unique. This system would be most desirable as a fully-automated, remotely controlled, mobile system that can be taken directly to where stranded wells are located. It is designed for mobile, medium-scale installation, which can be economically practical because of its radical simplicity and because it has freed itself from the requirements of oxygen and steam. The system is readily controllable in a small-scale system, and fully automated to lessen the labor burden. The inventors are going after economies not of scale, but economies of mass-production, to produce a standardized system that uses very little labor to control and operate. The system does not need any external utilities, as any unreacted carbon monoxide/hydrogen produced is more than sufficient to run the unit.

In short, the inventors have developed a mobile system that goes from flare gas—wet or dry—directly to methanol—without needing oxygen or steam.

Economic Estimates

One of many illustrative scenarios is presented here to demonstrate the potential profitability of the MENG system. In this scenario, dry methane gas is assumed to be the feedstock. Other configurations and use cases are also possible. This economic analysis is illustrative of the invention only and is not meant to limit the scope of the present invention. For the system size in Table 1, the value of the methanol product is about $2420 per day, or $883,000 per year. If it is using flare gas for feedstock, the cost of feedstock is zero. If is using commercial natural gas priced at $3 per MCF, the cost of feedstock is $504/day, or $184,000/year. If the unit is sold with a 6-year lease at 5% interest, the capital cost of the unit will be about $385,000 per year for the first six years, zero afterwards. Two full-time worker-equivalents, priced at $100,000 per year each, would be sufficient to operate the machine. Four cases have been defined by whether the unit is operating during the first six years, or afterwards, and whether the unit is using flare gas or commercial gas. These are examined in Table 3 as cases A, B, C, and D, respectively.

TABLE 3

Economic Estimates of the MENG Unit

|  | Case A | Case B | Case C | Case D |
|---|---|---|---|---|
| Feedstock | Flare Gas | Flare Gas | Commercial Gas | Commercial Gas |
| Period of Ops. | First 6 years | After 6 years | First 6 years | After 6 years |
| Annual Revenue | $883,000 | $883,000 | $883,000 | $883,000 |
| Capital Cost/yr | $385,000 | $0 | $385,000 | $0 |
| Feedstock Cost/yr | $0 | $0 | $184,000 | $184,000 |
| Labor Cost/yr | $200,000 | $200,000 | $200,000 | $200,000 |
| Net Profit/yr | $298,000 | $683,000 | $114,000 | $499,300 |

The company that manufactures the machine can make a two to one profit on each unit sold, while allowing the user to profit substantially starting on the very first day of operation, with profits growing substantially after six years when the machine is paid off.

However, Table 3 limits consideration of the value of the MENG unit to the value of the MENG product itself. In fact, in many cases there will be an additional value proposition, which may be substantially larger. This is because in many cases, those producing flare gas will be oil companies, whose wells may be shut down if their flaring is not eliminated. The value lost by losing oil production in this way may be an order of magnitude greater than the value of the methanol itself. For example, the inventors are acquainted with one oil producer who is currently flaring about 168 MCF of natural gas, who is being threatened with shutdown for this reason. If this occurs, the operator will lose its oil revenue, which is currently about $22,000 per day, or $8 million per year. Thus, the value of the MENG to such an operator could be many times greater than the calculations in Table 3, taken in isolation, would indicate.

On a per-unit basis, the MENG system would be capable of manufacturing methanol at a cost of $0.89/gallon ($0.29/kg) methanol during the first 6 years, and at a price of $0.31/gallon ($0.10/kg) methanol thereafter (after all the capital costs have been paid back). This corresponds to a methanol cost of about $0.61/gallon ($0.20/kg) methanol amortized over 12 years. This corresponds to a cost of about $1.20 per Gasoline-Gallon-Equivalent (GGE) amortized over 12 years, which is highly competitive.

Sulfur Removal Subsystem Embodiments

If necessary, and in some embodiments, as shown in FIG. 3, a desulfurization step can be added to remove any sulfur from the raw gas stream. The desulfurization subsystem would be applied to the gas stream upstream of the entire MENG process. Several alternative sulfur treatment and removal methods are possible according to various embodiments of the present invention. Dry sorbents may be used to capture sulfur in the feed gas. Calcium oxide, magnesium oxide, and sodium carbonate are example dry sorbents that are capable of trapping sulfur gases in solid form (as sulfates or sulfites, depending on the relative oxidation conditions). A fine sorbent can be injected into the feed gas, with resulting sulfur-containing solids then collected. In other embodiments, sulfur may also be removed by using a wet scrubber subsystem. Wet scrubbers can be configured in venturi, packed-column, or tray-type systems in which the feed gas is contacted with a scrubbing solution or slurry. The resulting scrubber solution or slurry must then be disposed.

That is, for sour flare gas that is rich in $H_2S$, the raw gas can be cleaned in a unit before further processing. For sulfur concentrations less than about 500 ppm, a disposable, solid iron-based sorbent would be optimal (low capital costs). The solid sorbent produces a recyclable iron sulfide waste. For higher sulfur concentrations, a liquid-based iron-chelate process would be appropriate. The liquid iron-chelate process produces an elemental sulfur filter cake by-product. Either by-product can be recycled or disposed off-site.

Modular System Design

The present invention may also be configured as a modular system, which may be created from modular units (for example, but not limited to, 170 mcf units). Each unit can run in parallel autonomously without interference. These units may be combined at the field depending on the application, and the requirements of a given user. Depending on the gas processing needs of a given site, multiple units may be combined to provide the necessary processing power. Similarly, as production declines or gas gathering lines are added, units can be removed and moved to new production locations.

Various Use Cases of the Present Invention

Some use cases of the present invention are now presented. These use cases are illustrative of the possible applications of the present invention and are not meant to be exhaustive or limiting.

FIG. 8 illustrates an example of a use case of the MENG in which a portion of the methanol stream is used as liquid fuel or transported to a remote location to power remote vehicle fleets. As shown, oil and associated gas (which is normally flared) is produced from well 802. The flare gas is taken to MENG unit 804, where it is turned into methanol 806, a portion of which can be buffered in buffer tank 808, then used to fill methanol storage cylinders 810. The stored methanol may be off-loaded directly to methanol-enabled vehicle tanks 812 for use in automotive vehicles, or loaded into methanol-enabled transport tankers 814, which may be transported to remote locations (for example, to fuel remote vehicle fleets).

Long-Felt, Unsolved Need for Cost-Effective, On-Site Gas Capture

As stated by a recent government-commissioned study, around 34% of North Dakota's produced associated gas was flared, nearly 340 million cubic feet per day (340 mmcf/day) in 2014, nearly double the 2011 flaring estimates of 190 million cubic feet per day (190 mmcf/day). (Source: Wocken, C. A.; Stevens, B. G.; Almlie, J. C.; Schlasner, S. M., *End-Use Technology Study—An Assessment of Alternative Uses for Associated Gas*, National Energy Technology Laboratory, Pittsburgh, Pa., April 2013, incorporated by reference in its entirety herein.) This U.S. Department of Energy study demonstrates the long-felt and unsolved need for mobile technology to address this issue. This study also shows that no existing technology can produce a useable and transportable liquid stream from raw flare gas, wet or dry, which is one innovative aspect of the present invention. This discussion is merely illustrative and exemplary, and is not intended to limit the scope of the present invention or its application or uses.

Several random samples of Bakken region wellhead gas quality data are presented in Table 3 (Source: Wocken, C. A.; Stevens, B. G.; Almlie, J. C.; Schlasner, S. M., *End-Use Technology Study—An Assessment of Alternative Uses for Associated Gas*, National Energy Technology Laboratory, Pittsburgh, Pa., April 2013). This high NGLs content typically corresponds with high Wobbe index (higher energy content of 1300-2000 BTU/cf) when compared to residential pipeline gas (~1000 BTU/cf). All of these can be converted to methanol directly, or after separation of the higher carbon components from methane, with the methane converted to methanol.

TABLE 3

Selected Flare Gas Data from Wellheads in the Bakken Formation

| | Wellhead Sample: | | |
|---|---|---|---|
| | Sample 1 | Sample 2 | Sample 3 |
| Methane, mol % | 70.23 | 48.07 | 73.93 |
| Ethane, mol % | 13.94 | 18.78 | 13.25 |
| Propane, mol % | 6.7 | 14.87 | 5.55 |
| Butane + (C4+), mol % | 5.5 | 16.38 | 4.32 |
| $CO_2 + N_2$, mol % | 3.44 | 1.72 | 2.87 |
| $H_2S$ | 0.19 | 0.18 | 0.08 |
| Wobbe Index, BTU/scf | 1470 | 1712 | 1454 |
| Methane No. (MN) | 53.2 | 43.5 | 56.1 |

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

While the present invention has been particularly shown and described with reference to embodiments thereof, it will be understood by those skilled in the art that various other changes in the form and details may be made without departing from the spirit and scope of the present invention.

What is claimed is:

1. A method for converting raw natural gas into methanol using air as a source of oxygen, comprising:
   a syngas generation step for generating syngas from the raw natural gas and the air in an air reforming unit, wherein the syngas comprises carbon monoxide, hydrogen, and nitrogen;
   a syngas compression step for compressing the syngas that comprises the carbon monoxide, the hydrogen, and the nitrogen;
   a methanol synthesis step for synthesizing methanol from the syngas over a catalyst bed; and
   a power generation step for using unreacted carbon monoxide and hydrogen in the syngas to generate power, wherein some of the power is used to power the syngas compression step, and wherein unreacted nitrogen is returned to atmosphere.

2. The method of claim 1, further comprising: removing sulfur from the raw natural gas.

3. The method of claim 1, wherein the syngas generation step comprises reforming the raw natural gas and the air in a presence of a steam reforming catalyst.

4. The method of claim 1, wherein air enriched in oxygen is used to increase concentrations of the carbon monoxide and the hydrogen in the syngas.

5. The method of claim 1, wherein water is added to the air reforming unit to prevent catalyst coking.

6. The method of claim 5, wherein the water is recycled to the air reforming unit from a condenser downstream from an air recycling unit.

7. The method of claim 5, wherein the water is converted to steam inside the air reforming unit.

8. The method of claim 1, wherein a gas mixer mixes the raw natural gas and the air before these gases pass through a syngas catalyst bed in the air reforming unit.

9. The method of claim 1, wherein the raw natural gas and the air are preheated to improve the carbon monoxide yield.

10. The method of claim 1, wherein the catalyst bed comprises a syngas-to-methanol synthesis catalyst.

11. The method of claim 10, wherein the syngas-to-methanol synthesis catalyst comprises Cu—ZnO.

12. The method of claim 1, wherein the methanol is removed from an effluent of the catalyst bed.

13. The method of claim 12, wherein a heat exchanger is used to cool effluent gases to a temperature at which most of methanol vapor condenses to liquid, a phase separator to separate liquid methanol from gases, and a component for draining liquid methanol.

14. The method of claim 1, wherein the syngas is preheated before the catalyst bed.

15. The method of claim 1, wherein energy is exchanged between streams entering and exiting the catalyst bed to reduce duties on syngas preheating and syngas cooling.

16. The method of claim 1, wherein energy released in the methanol synthesis step is removed from the catalyst bed.

17. The method of claim 1, wherein the carbon monoxide conversion to methanol is enhanced by using a recycle blower.

18. The method of claim 1, wherein the carbon monoxide conversion to methanol is enhanced by using cascading catalyst beds with methanol being removed between the cascading catalyst beds.

19. The method of claim 1, wherein the power is generated by combusting the unreacted carbon monoxide and hydrogen in a spark ignited internal combustion engine, and using engine power to drive an electric generator.

20. The method of claim 1, wherein some of the syngas is recirculated back to the syngas generating step to prevent hot spots in the catalyst bed.

21. The method of claim 1, wherein the syngas generation step utilizes a pressure range of 0.1 and 10 bar.

22. The method of claim 21, wherein a temperature of the syngas generation step is between 400 to 1000° C. (673-1273 K).

23. The method of claim 21, wherein a temperature of the syngas generation step is above 700° C. (973 K).

24. The method of claim 1, wherein the syngas compression step compresses the syngas to about 600 psi (41 bar).

25. The method of claim 1, wherein the methanol synthesis step utilizes a pressure range of 10 and 1,000 bar.

26. The method of claim 25, wherein a temperature of the methanol synthesis step at an inlet of the catalyst bed is between 170 and 250° C. (443-523 K).

* * * * *